US010207067B2

(12) United States Patent
Toksoz et al.

(10) Patent No.: US 10,207,067 B2
(45) Date of Patent: Feb. 19, 2019

(54) BLISTER ADVANCEMENT MECHANISM COMPRISING AN ACTUATOR PLATE

(71) Applicant: Arven Ilac Sanayi Ve Ticaret Anonim Sirketi, Istanbul (TR)

(72) Inventors: Zafer Toksoz, Istanbul (TR); Umit Cifter, Istanbul (TR); Ali Turkyilmaz, Istanbul (TR); Onur Mutlu, Istanbul (TR)

(73) Assignee: Arven Ilac Sanayi Ve Ticaret Anonim Sirketi, Istanbul (TR)

( * ) Notice: Subject to any disclaimer, the term of this patent is extended or adjusted under 35 U.S.C. 154(b) by 701 days.

(21) Appl. No.: 14/403,435

(22) PCT Filed: May 21, 2013

(86) PCT No.: PCT/TR2013/000171
§ 371 (c)(1),
(2) Date: Nov. 24, 2014

(87) PCT Pub. No.: WO2013/176643
PCT Pub. Date: Nov. 28, 2013

(65) Prior Publication Data
US 2015/0174345 A1 Jun. 25, 2015

(30) Foreign Application Priority Data

May 25, 2012 (TR) .................................. 2012/06167
Feb. 8, 2013 (TR) .................................. 2013/01562
(Continued)

(51) Int. Cl.
*A61M 15/00* (2006.01)

(52) U.S. Cl.
CPC .... *A61M 15/0053* (2014.02); *A61M 15/0021* (2014.02); *A61M 15/0043* (2014.02);
(Continued)

(58) Field of Classification Search
CPC .......... A61M 15/0001; A61M 15/0006; A61M 15/0021; A61M 15/0033; A61M 15/0026;
(Continued)

(56) References Cited

U.S. PATENT DOCUMENTS 3,924,476 A 12/1975 Wolcott
2007/0119450 A1* 5/2007 Wharton ............... A61M 15/00
128/200.23

FOREIGN PATENT DOCUMENTS

WO 2010114504 A1 10/2010
WO 2010114505 A1 10/2010
(Continued)

OTHER PUBLICATIONS

International Search Report in PCT/TR2013/000171, dated Oct. 14, 2013.

*Primary Examiner* — Gregory Anderson
*Assistant Examiner* — Margaret Luarca
(74) *Attorney, Agent, or Firm* — Liang & Frank LLP

(57) ABSTRACT

The present invention relates to improvements made in the blister advancement mechanism of dry powder inhaler devices. A dry powder inhaler device mechanism comprising an actuator plate and a transmission wheel is provided.

11 Claims, 14 Drawing Sheets

(30) Foreign Application Priority Data

| Feb. 15, 2013 | (TR) | ................................. 2013/01847 |
| Feb. 19, 2013 | (TR) | ................................. 2013/01950 |
| Mar. 26, 2013 | (TR) | ................................. 2013/03661 |
| Apr. 29, 2013 | (TR) | ................................. 2013/05053 |
| May 9, 2013 | (TR) | ................................. 2013/05562 |
| May 13, 2013 | (TR) | ................................. 2013/05655 |

(52) U.S. Cl.
CPC .... *A61M 15/0051* (2014.02); *A61M 15/0055* (2014.02); *A61M 15/0026* (2014.02); *A61M 2202/064* (2013.01); *A61M 2205/103* (2013.01); *A61M 2205/19* (2013.01)

(58) Field of Classification Search
CPC .......... A61M 15/0043; A61M 15/0051; A61M 15/0053; A61M 15/0055; A61M 2205/103; A61M 2205/19
USPC .................................................... 128/203.15
See application file for complete search history.

(56) References Cited

FOREIGN PATENT DOCUMENTS

| WO | 2010114506 A1 | 10/2010 |
| WO | 2011129788 A1 | 10/2011 |

\* cited by examiner

BLISTER ADVANCEMENT MECHANISM COMPRISING AN ACTUATOR PLATE

CROSS REFERENCE TO RELATED APPLICATIONS

This application is a U.S. national phase of international application, PCT/TR2013/000171, filed May 21, 2013, which claims the priority of applications, Nos. TR2012/06167, filed May 25, 2012; TR2013/01562, filed Feb. 8, 2013; TR2013/01847, filed Feb. 15, 2013; TR2013/01950, filed Feb. 19, 2013; TR2013/03661, filed Mar. 26, 2013; TR2013/05053, filed Apr. 29, 2013; TR2013/05562, filed May 9, 2013, and No. TR2013/05655, filed May 13, 2013, the disclosures of which patent applications are incorporated by reference herein.

FIELD OF INVENTION

The present invention relates to a device for administering dry powder inhalation drugs.

The present invention particularly relates to improvements made in the blister advancement mechanism of dry powder inhaler devices.

PRIOR ART

Diseases such as asthma, bronchitis, and COLD (Chronic Obstructive Lung Disease) substantially decrease the quality of human life, despite the developments which have been carried out in the diagnosis and therapy thereof in the recent years. It has been proposed to administer medicaments via inhalers for optimizing the treatment of such diseases. The inhaler route of treatment is the most preferred one and it is expected to remain so, as the first option, in the future. The most important advantage of using medicaments via inhalation is based on providing a more efficient therapy by making use of a lower amount of medicaments, delivering higher concentrations of medicaments to the airways, and particularly decreasing the systemic side effects of medicaments. The most important causes of the lack of a satisfactory control of patients albeit the presence of quite efficient treatments against respiratory tract diseases are stated to be as the noncompliance, arising from the inefficient use of inhalers and from inadequate compliance to the physician-recommended treatments.

There have been developed various inhaler devices for administering inhalation drugs nowadays. These devices are basically classified into two groups, i.e. metered dose inhalers and dry powder inhalers. Such type of devices are structurally provided with such basic components as an actuator, counter, housing, lid, lock, etc. Additionally, powder inhalation drugs are kept in reservoirs or containers such as blisters, capsules, etc. Blisters are structured from two basic parts, a main layer provided with cavities holding the drug, and a strippable protective layer.

Such devices comprise an outer body and a lid provided thereon, an inner body disposed in the outer body, a blister strip placed in the inner body, a lower holder or reservoir receiving the strip in a rolled form, as well as gears and a gear set connected to each other in a functionally compatible manner to actuate the blister strip so that the main layer thereof comprising the cavities is wound and stored after it is separated into its layers. Push members or trigger mechanisms have been developed to actuate this mechanism.

In inhaler devices with a plurality of blisters, a force is exerted to the mechanism actuating the blister by means of the trigger or the push member such that the mechanism is actuated. In practice, however, various problems are encountered in the mechanisms. Some of these are encountered in the triggers actuating the mechanism. These triggers are disadvantageous in terms of use difficulty, and require an extra movable volume on the exterior of the inhaler device. The linear motion of trigger mechanisms, which are advantageous in terms of volume and are slid into the interior of the device, is converted into a rotational motion by means of a gear to which it is connected. In the applications WO2010114506, WO2010114505, for instance, the linear motion performed by a trigger is converted into a rotational motion by means of a wheel. This trigger is slid into a slot in the body of the inhaler device to perform axial motion, and the force generated by this motion is transferred to a blister advancement mechanism by means of a gear with which it meshes. However, the gears providing the transmission and conversion of this motion are exposed to overloads. Additionally, losses are encountered in force transmission when (an) extra gear(s) is/are used. The elimination of this loss, in turn, requires the exertion of an extra amount of force. Another drawback is that slackness occurs between the gears and the contact surfaces. This slackness and extra force exertion, in turn, result in a greater problem in that the gears and wheels in the mechanism become worn out or even break.

The use of the currently available inhaler devices necessitates certain training and practice. The development of inhaler devices always occurs in the form of practical systems, providing the patients with improved convenience of use. Selecting the proper device for a respective patient is also an important issue. Many criteria, such as a patient's cognitive and physical efficiency, ease of use, safety and price, etc. are considered while a device is selected.

In result, there is a novelty required in the field of inhaler devices, providing high-accuracy operation, advantages in terms of cost, volume, and use, as well as minimizing the failures and damages which can occur in the device.

OBJECTS AND BRIEF DESCRIPTION OF INVENTION

The present invention relates to an improved inhaler device for use with dry powder inhaling purposes, eliminating all aforesaid problems and brining additional advantages to the relevant prior art.

Accordingly, the main object of the present invention is to provide a dry powder inhaler device, which can be operated at a desired accuracy, can peel off a blister for use, and can perform this process faultlessly as compared to similar devices.

Another object of the present invention is to reduce the amount of force to be exerted to the trigger of the device to operate the same.

Another object of the present invention is to prevent the wearing or breaking of the components in the mechanism as a result of reducing the amount of force exerted to the trigger and thus to the gears and the gear mechanism.

In order to achieve the objects referred to above and to emerge in the following detailed description, a dry powder inhaler device is developed which comprises a body and a trigger moving on an axial/linear direction in the body, a main drum into which a blister strip having drug-carrying cavities is placed, a gear set which enables to release a drug in the next cavity of the blister strip to be administered with rotating the main drum and around which a protective layer of the blister strip is wound, and additional gears which are in connection with the main drum and around which a main layer of the blister strip is wound.

A preferred embodiment according to the present invention is characterized by comprising an actuator plate having a first end connected to the trigger and a second end comprising a socket with a size sufficiently large to receive a transmission wheel therein, a series of teeth which are aligned in the socket of the actuator plate on the axial/linear direction in which the trigger moves, and a transmission wheel connected to the teeth in the socket.

A preferred embodiment according to the present invention comprises barriers on the inner surface of the body to restrict the amount of displacement of the actuator plate.

In a preferred embodiment according to the present invention, the actuator channel is disposed between the main drum and the trigger.

In a further preferred embodiment according to the present invention, the transmission wheel comprises a toothless surface section.

In a preferred embodiment according to the present invention, the main drum is disposed on the transmission wheel which meshes with the straight teeth on the socket of the plate.

A preferred embodiment according to the present invention comprises a pretensioned spring which restores the trigger to its initial position after it is pushed in axially and released by a user.

Structural and characteristic features, and all advantages of the present invention shall be made clear by means of annexed figures described here below and a detailed description written by making references to said figures; therefore, the present invention must be evaluated by taking into consideration these figures and the detailed description as well.

REFERENCE NUMBERS IN FIGURES

Figure 1:
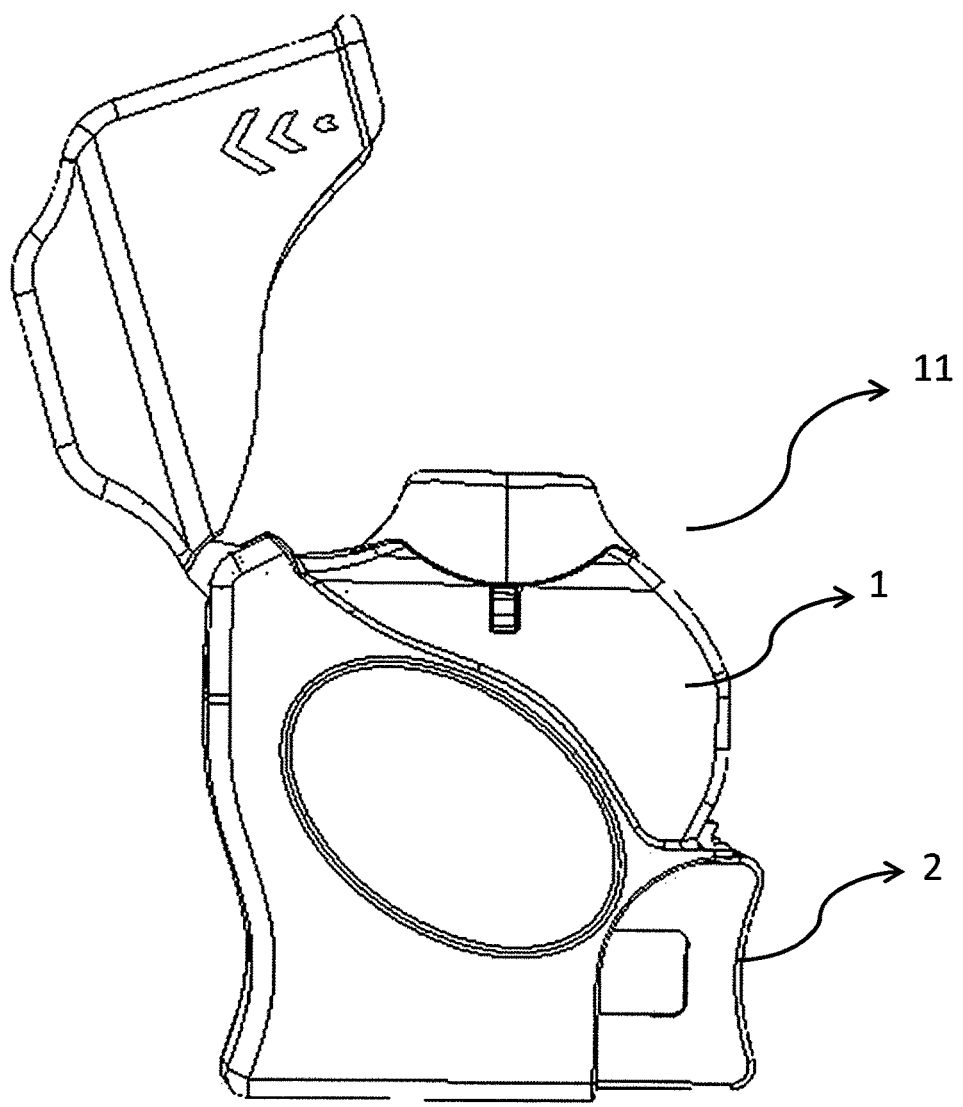
FIG. 1 is an illustration of an exemplary embodiment according to the present invention.
Figure 2:
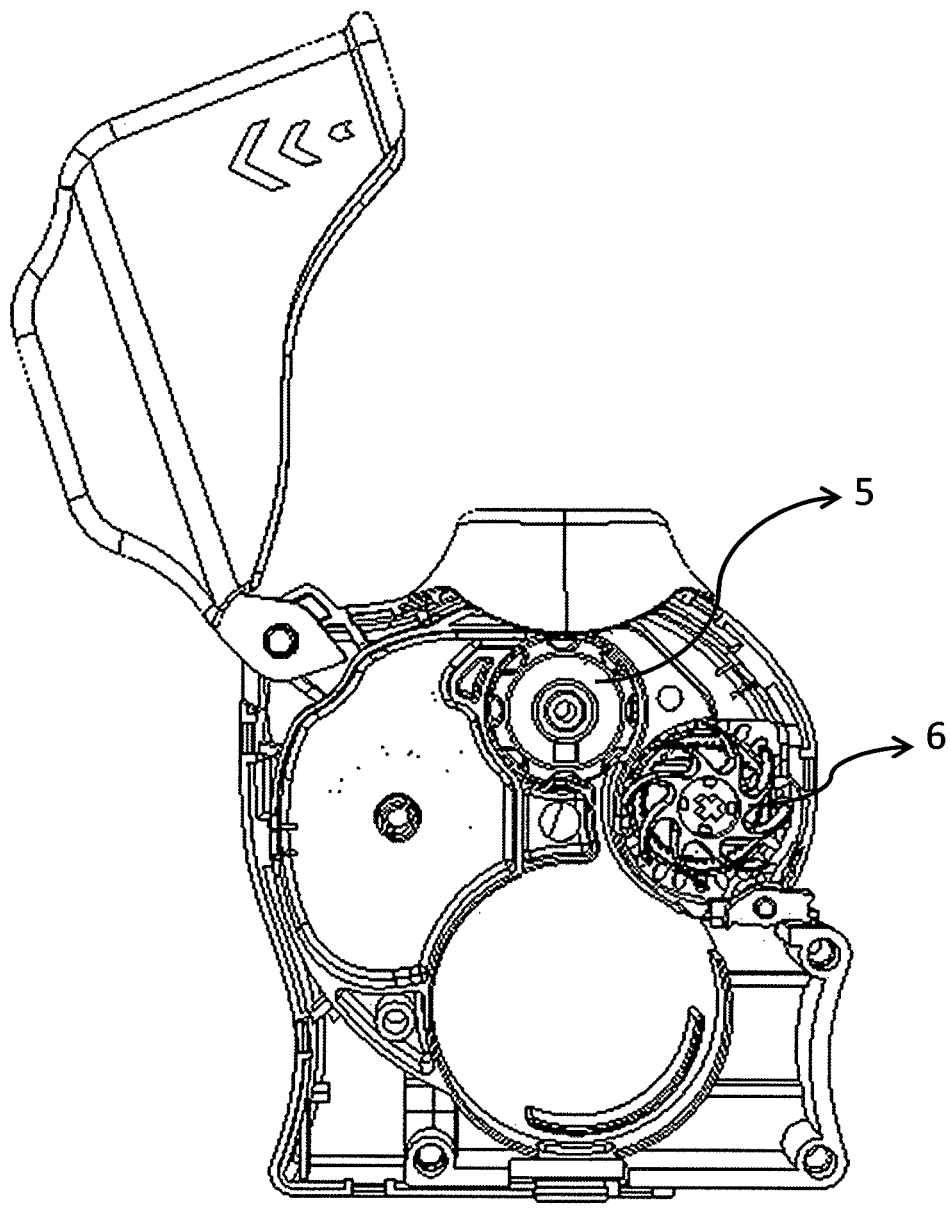
FIG. 2 is a representative embodiment of an outer body and an inner body according to the present invention.

1. Outer body
2. Trigger
3. Cavity
4. Blister
5. Main drum
6. Blister cover upper winding gear
7. Blister cover central winding gear
8. Blister cover lower winding gear
9. First additional gear
10. Second additional gear
11. Inhaler device
12. First end of the actuator plate
13. Second end of the actuator plate
14. Socket
15. Actuator plate
16. Linear/straight teeth
17. Transmission wheel
18. First barrier of the body
19. Second barrier of the body
20. Toothless surface of the transmission wheel
21. Toothed surface of the transmission wheel
22. Spring
23. Inner body
24. Lower reservoir
25. Left medial reservoir
26. Right medial reservoir
27. Upper reservoir

DETAILED DESCRIPTION OF INVENTION

In the following detailed description, an inhaler device (11) according to the present invention shall be described illustratively by making references to annexed figures, only to make it clear without imposing any restrictions thereon.

An outer body (1) of the inhaler device (11) according to the present invention as illustrated in FIGS. 1, 2, 4, 11a, 11b, 12a, 12b is obtained by assembling two compatible parts together. The interior of said parts comprises both fastening tabs to fasten them together, and reservoirs and pins, allowing the placement of the mutually connected main drum and transmission wheel (5, 17) and the mutually connected blister cover winding gear set (6, 7, 8) in the outer body (1). The upper part of the body is provided with a mouthpiece having a drug outlet opening. The lower part of the body is provided with a trigger (2) slid into the body.

Figure 10:
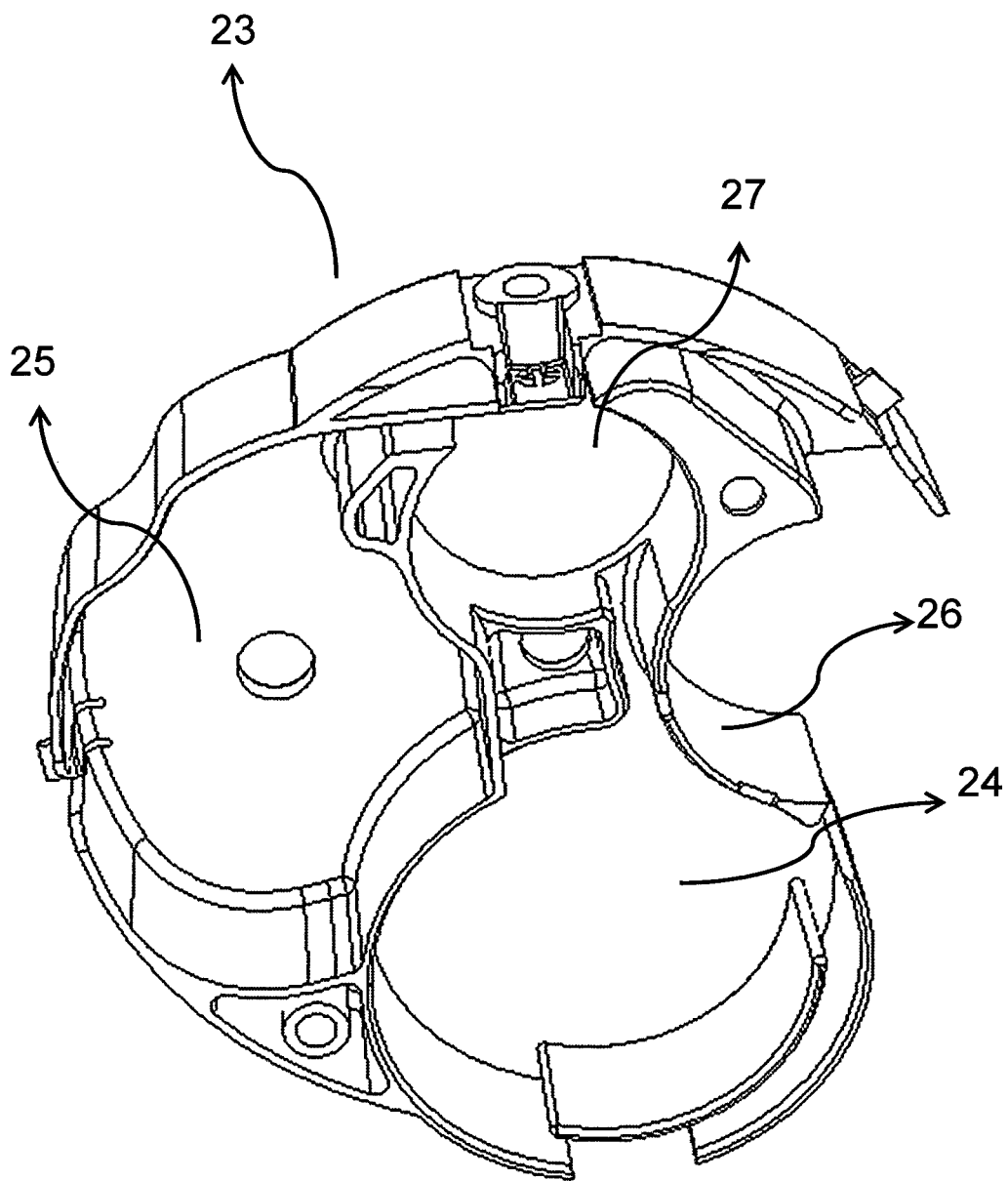
FIG. 10 is a representative embodiment of the inner body according to the present invention.

An inner body (23) is positioned in the interior of the outer body (1) to place a blister (4) therein, as illustrated in FIG. 10. This single-piece body (23) comprises lower, left and right medial and upper reservoirs (24, 25, 26, 27), respectively, along with recessed surfaces and fastening tabs. An unused blister (4) is stored in the lower reservoir (24), this strip-shaped blister (4) being extended along intermediate channels and subsequently separated into two parts, i.e. a main layer and a protective layer, by means of the mechanism. The main layer with one end fastened to a second additional gear (10) is stored in the left medial reservoir (25) where this second additional gear (10) is positioned. The end of the protective layer, in turn, is fastened to a pin provided on the central winding gear (7).

Figure 3:
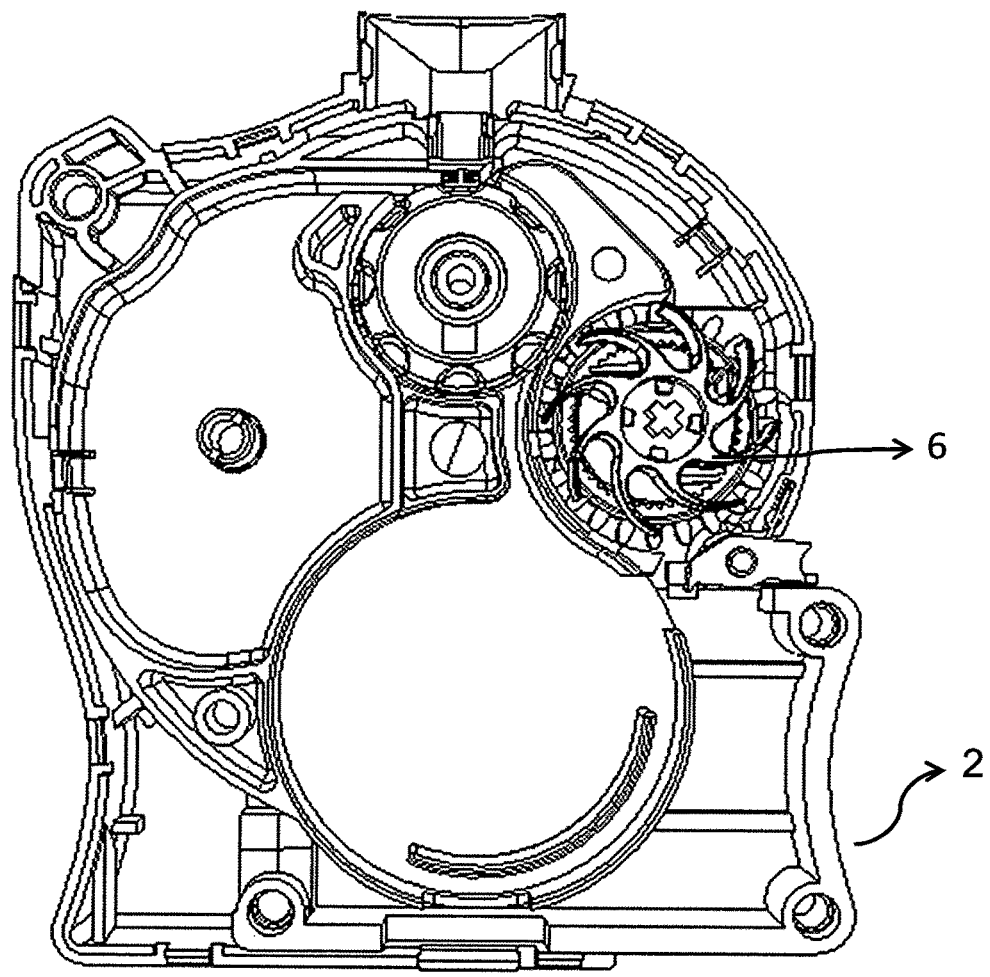
FIG. 3 is a representative embodiment of the outer body, inner body, and a mechanism according to the present invention.
Figure 4:
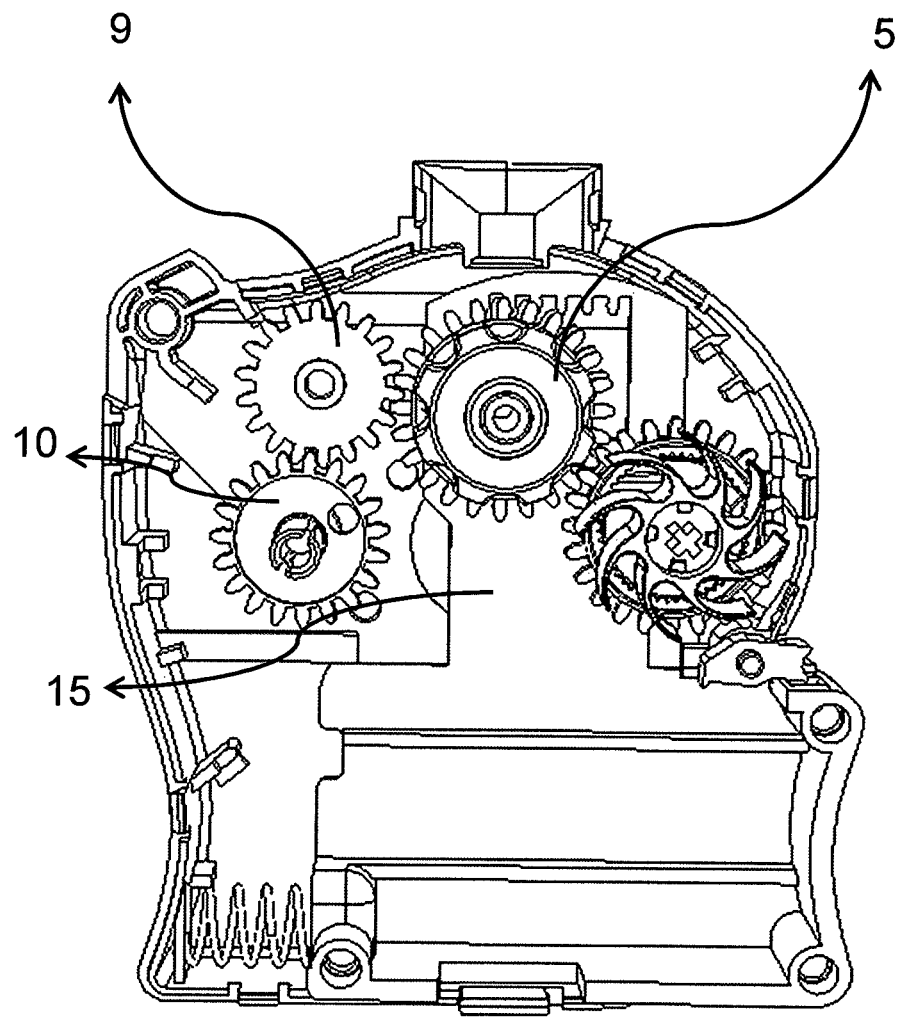
FIG. 4 is a representative embodiment of the outer body and the mechanism according to the present invention.
Figure 5:
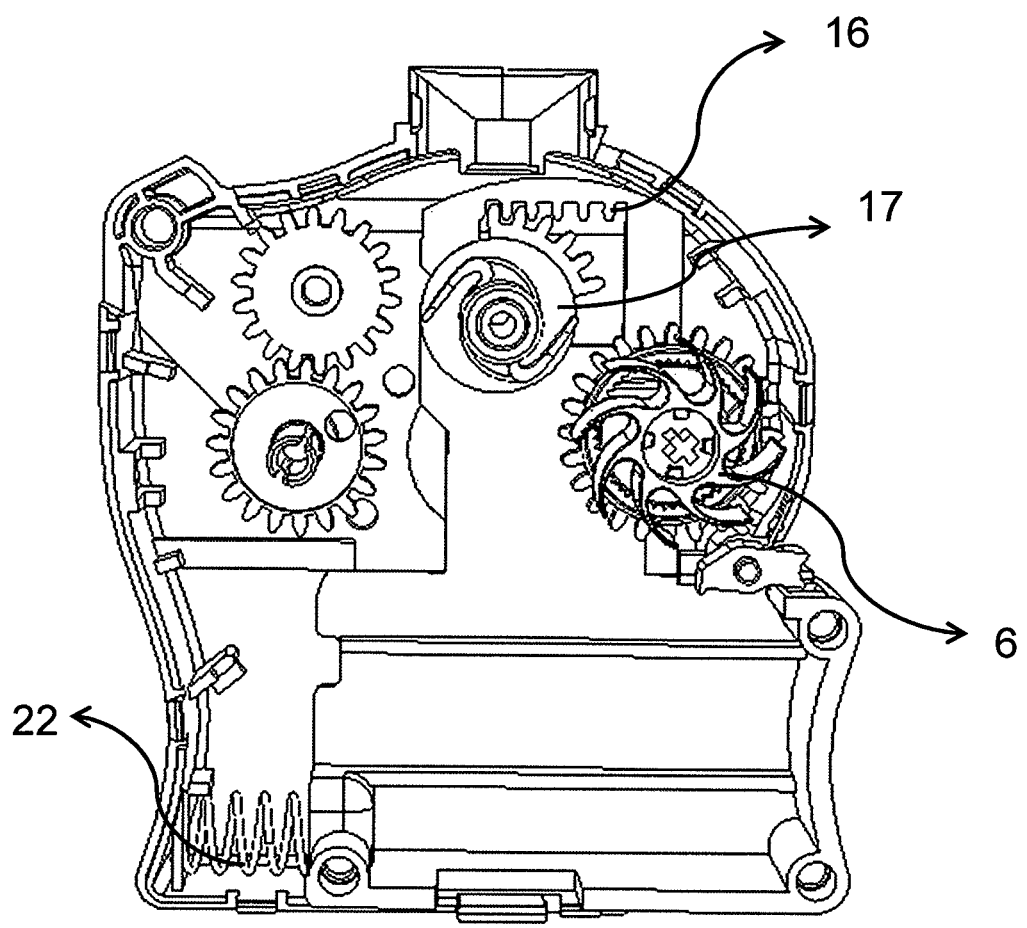
FIG. 5 is a representative embodiment of the outer body and the mechanism according to the present invention.
Figure 6:
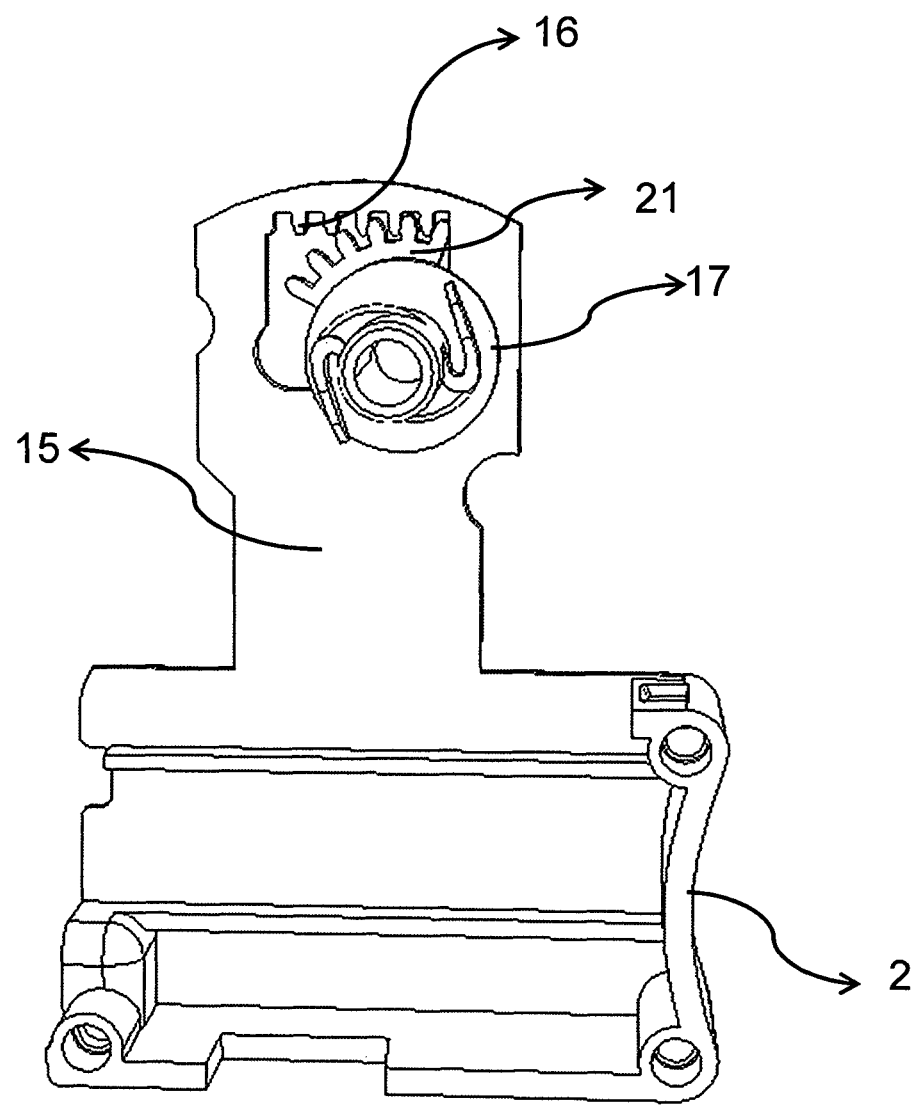
FIG. 6 is a representative embodiment of the mechanism according to the present invention.
Figure 7:
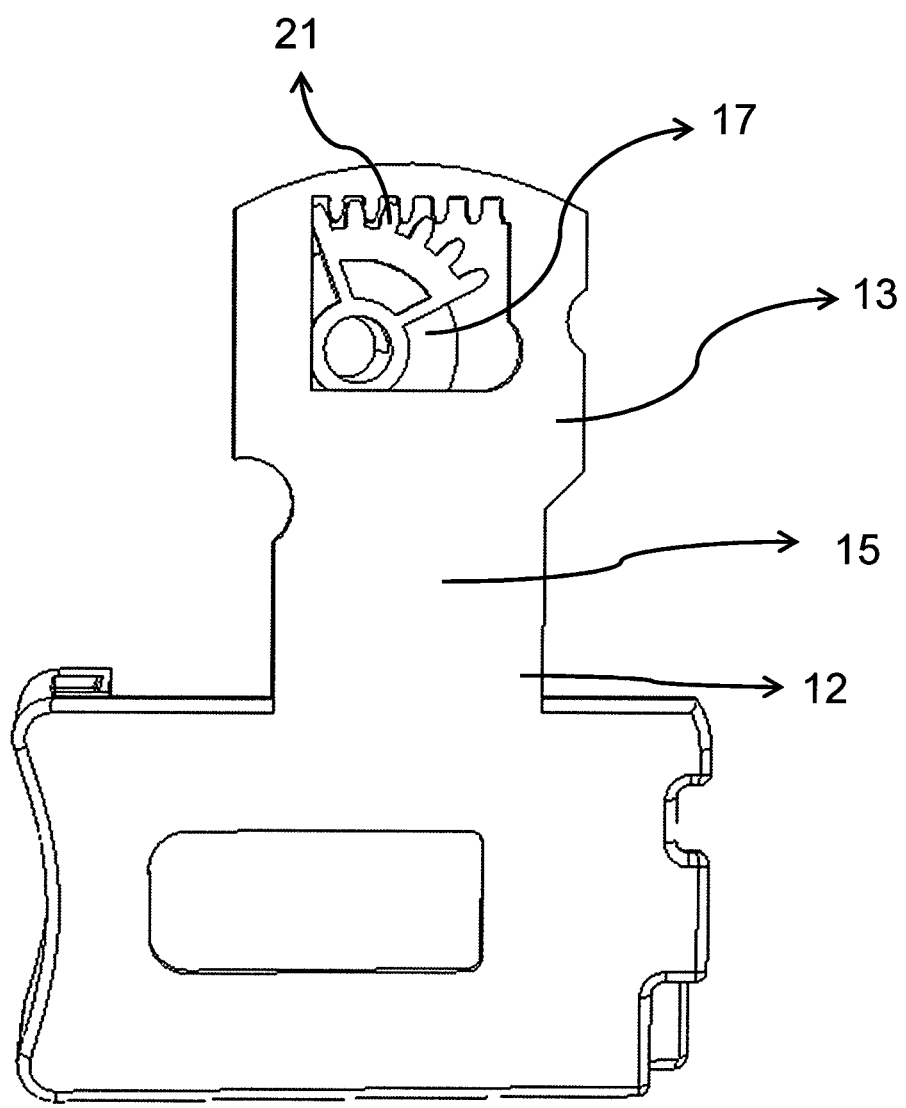
FIG. 7 is a representative embodiment of the mechanism according to the present invention.
Figure 8:
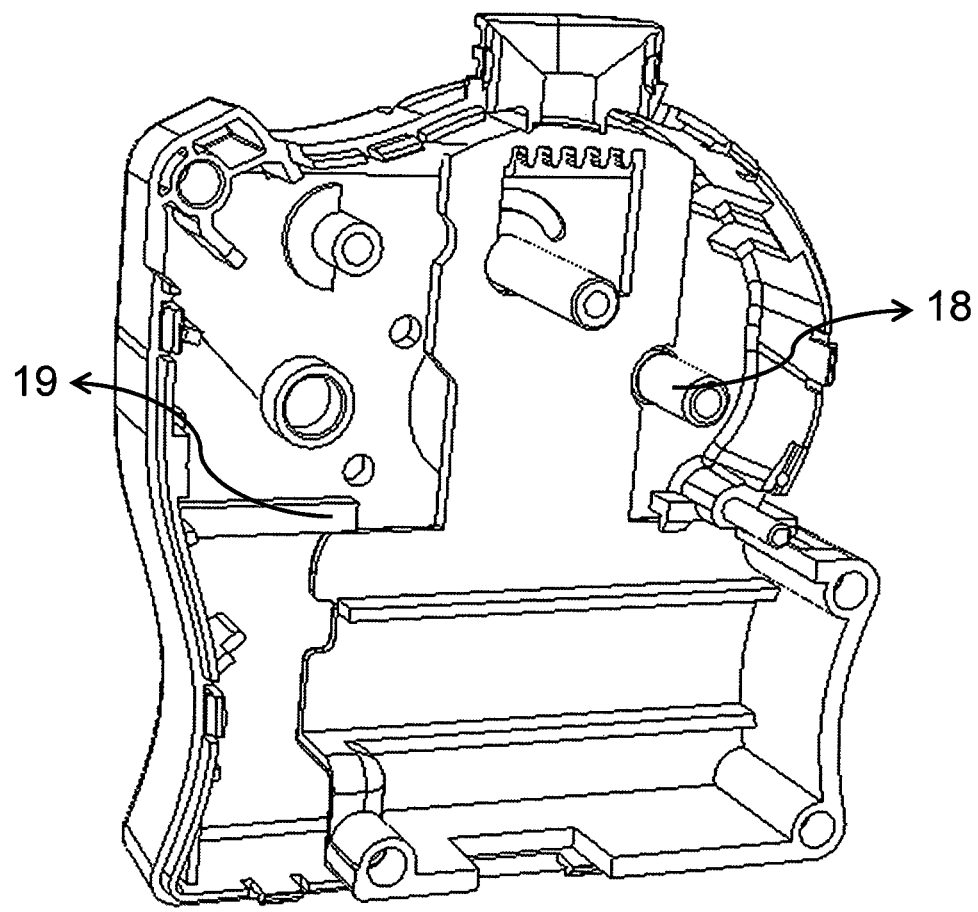
FIG. 8 is a representative embodiment of the mechanism according to the present invention.
Figure 9:
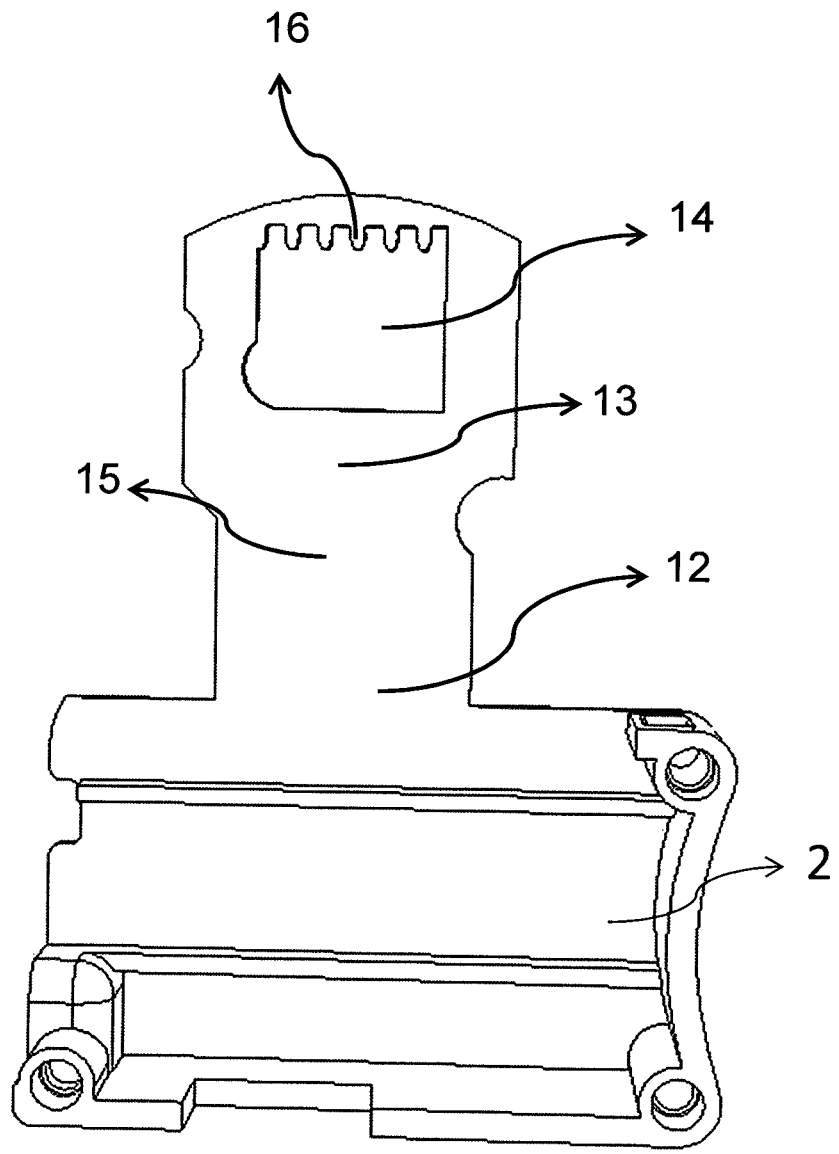
FIG. 9 is a representative embodiment of the trigger with actuator plate according to the present invention.

As illustrated in FIGS. 3 and 4, at the beginning of the blister (4) advancement mechanism is provided a trigger (2), slid into a lower side of said outer body (1). The trigger (2) is capable to perform an axial/linear motion in the inner part of the body (1). A grip surface provided on the exterior of the trigger (2), which is the surface by which a user exerts force to push in said trigger, is formed in an incurved manner to provide ease of use. A spring (22) is positioned between the trigger (2) and an inner surface of the outer body (1), this spring becoming compressed (i.e. loaded) when the trigger (2) is pushed into the body (1). The spring (22) has a helical form.

As illustrated in FIGS. 4, 5, 6, 7 and 11a, an actuator plate (15) is provided having a first end (12) connected to the trigger and a second end (13) comprising a socket (14). This socket is formed with a size which is sufficiently large to receive a wheel therein. Straight teeth (linear teeth) (16) are provided in the socket (14) of the actuator plate (15), these teeth being aligned in the axial/linear direction in which the trigger is moved. The socket has a rectangular form with the teeth being aligned on an upper edge of the socket. A transmission wheel (17) is positioned in the socket. The wheel (17) is connected to a pin fixed to the body in a moving manner from a central point thereof. This connection provides the wheel with a rotational motion only. A section of the periphery of the wheel (17) is provided with a series of teeth, whereas the remaining peripheral surface (20) thereof is toothless. The toothed surface (21) of the wheel meshes with the straight teeth (16) of the actuator plate (15). The toothed surface (21) of the wheel which meshes with the straight teeth provides a rotating function. The toothless surface section (20), in turn, provides for the rotation without contacting any surface within the socket and makes it possible to keep the volume of the socket at an acceptable level. Barriers (18, 19) are formed on the inner surface of the body on both longitudinal edges of the actuator plate. The wheel (17) is engaged to a main drum (5). The main drum (5) is mounted over the wheel (17) so as to move in the same way with the wheel.

According to the details given above, the operation of the device according to the present invention is as follows. Following the opening of the lid of the device, a force is exerted by the user to the grip surface of the trigger (2). Then the trigger (2) is slid into the interior of the body (1). With the axial/linear motion of the trigger (2), the actuator plate (15) coupled to the trigger is set into motion as well. Thus, the transmission wheel (17) connected to the straight teeth of the actuator plate is set into rotation. With the movement of the wheel (17), the main drum (5) disposed over the wheel is rotated so as to rotate the gears with which it meshes. In this manner, a blister placed on the gears is moved and the cavities (3) of the blister are opened.

Figure 11A:
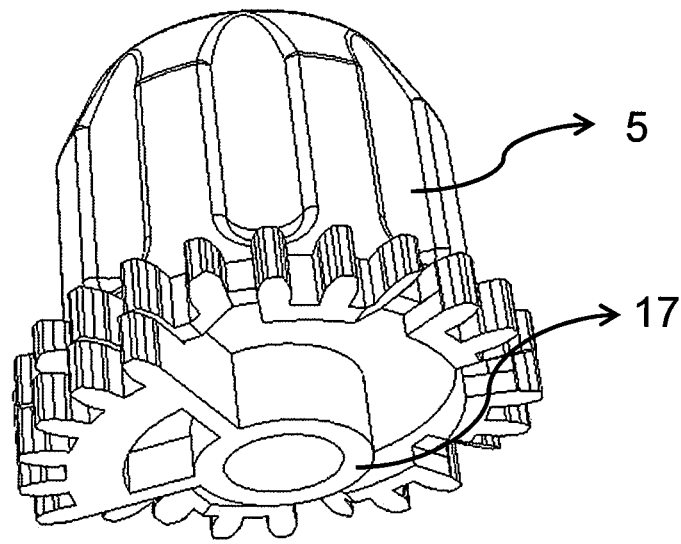
FIG. 11a is a representative embodiment of a main drum and the transmission wheel according to the present invention.
Figure 11B:
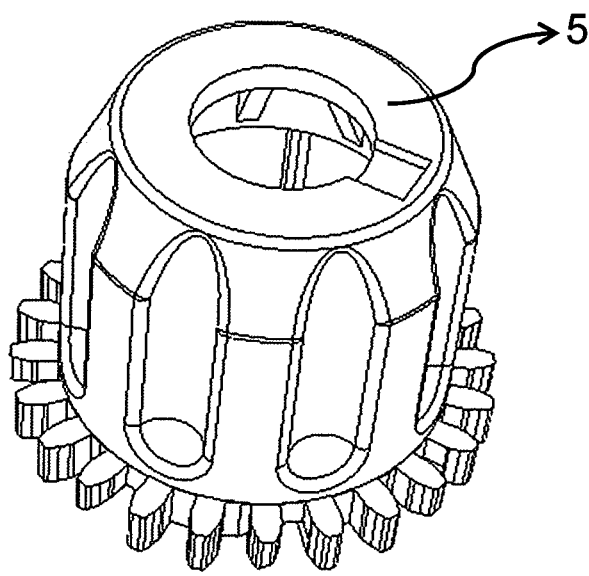
FIG. 11b is a representative embodiment of a main drum according to the present invention
Figure 12A:
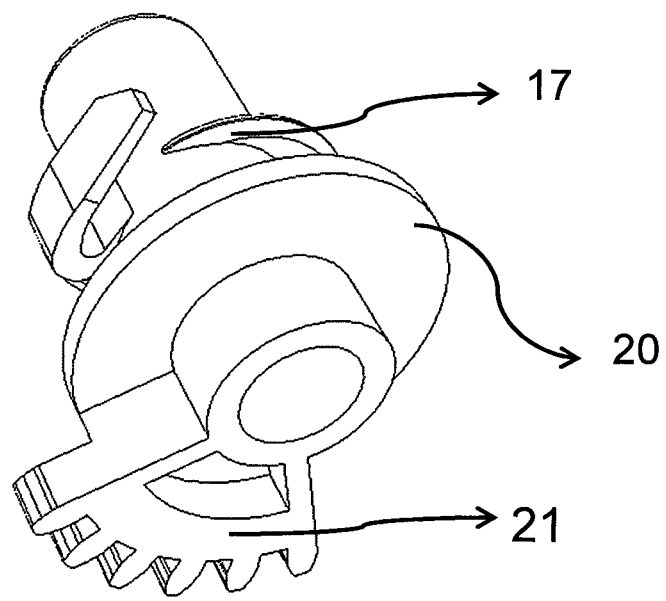
FIG. 12a is a representative embodiment of a transmission wheel according to the present invention.
Figure 12B:
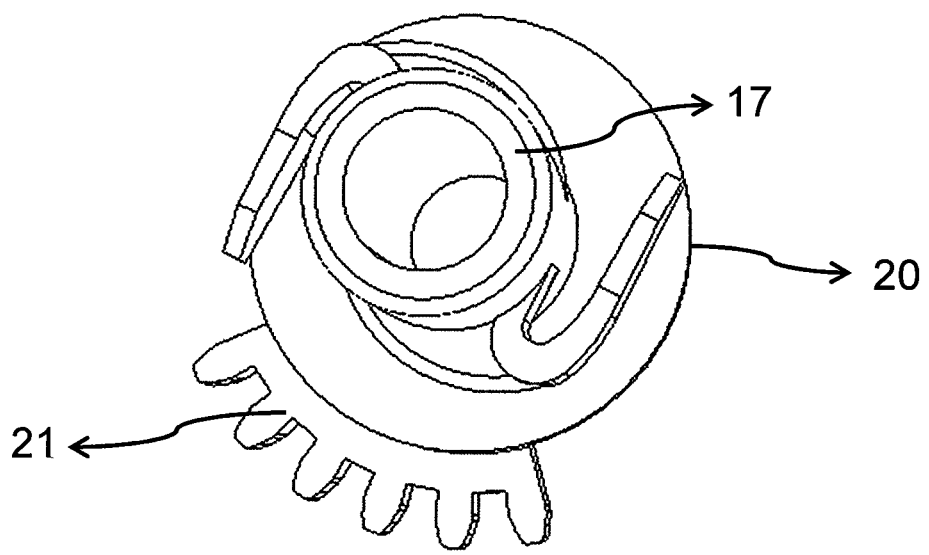
FIG. 12b is a representative embodiment of a transmission wheel according to the present invention.
Figure 13A:
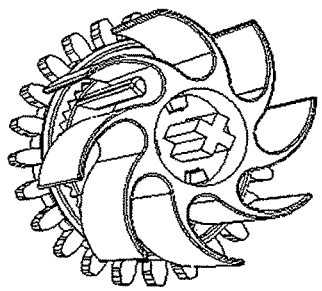
FIG. 13a is a representative embodiment of blister cover winding gears according to the present invention.
Figure 13B:
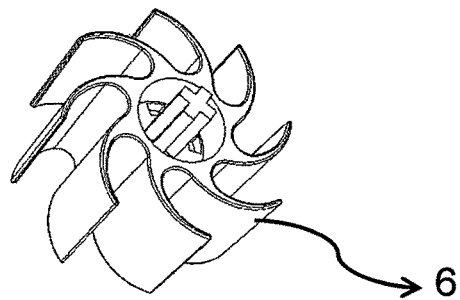
FIG. 13b is a representative embodiment of a blister cover upper winding gear according to the present invention.
Figure 13C:
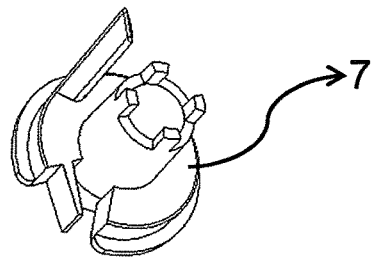
FIG. 13c is a representative embodiment of a blister cover central winding gear according to the present invention.
Figure 13D:
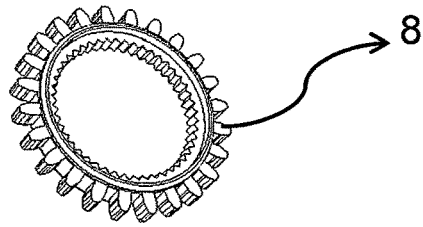
FIG. 13d is a representative embodiment of a blister cover lower winding gear according to the present invention.
Figure 14:
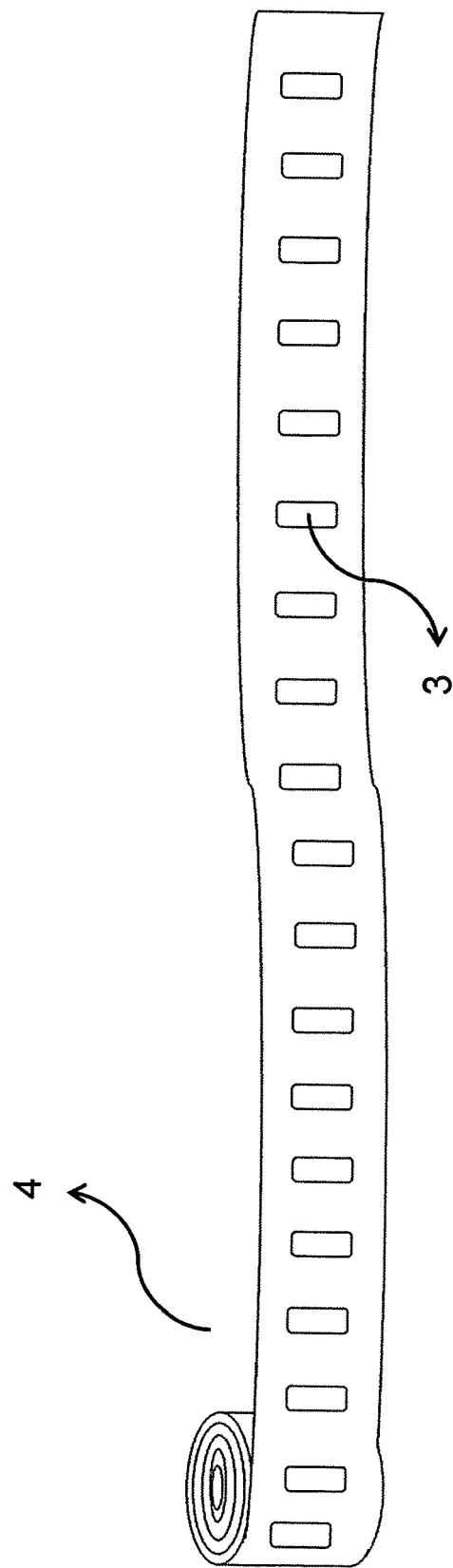
FIG. 14 is a representative embodiment of a blister according to the present invention.

As illustrated in detail in FIG. 11a, the main drum (5) moves on a single direction and provides only the advancement of the blister (4). The transmission wheel (17) below the main drum is capable to rotate forward and backward.

The transmission wheel (17) transmits this motion to the main drum (5) and to the first and second additional gears (9, 10). While the transmission wheel and the main drum (17, 5) rotate counterclockwise, the blister cover lower winding gear (8) and the blister cover central and upper winding gears (7, 6) disposed above the lower winding gear rotate clockwise. The blister (4) in contact with these gears is advanced in the channels of the inner body (23), is passed through and stripped or peeled off between the gear sets so that the drug in the respective cavity is released. The main layer of the blister, now separated into two parts, is rolled in the left medial reservoir (25), whereas the protective or cover layer of the blister is wound around the blister cover upper gear (6).

As a result of sliding the trigger (2) into the interior of the outer body (1), a retaining groove provided on the trigger (2) is coupled and fastened to a locking clips lug provided just over the groove, resulting in the administration of a single dose of medicament. Keeping this slide-in action until the locking position is achieved ensures a complete peeling-off of the blister and an accurate administration of the required dosage amount. As a result of this locking effect, the trigger (2) becomes retained and it remains out-of-use for a short period of time. This slide-in action also causes the spring (22) to become compressed between the trigger (2) and the interior of the outer body (1).

After the user inhales the powder drug, he/she closes the lid of the device, so that a tip part of the lid exerts force to a rear part of the locking clips, the tip thereof is lifted above, and the clips lug and the retaining groove are detached from each other. As a result of this, the compressed spring (22) rotates the wheel (17) backward and makes the mechanism move backward too. Thus, the device is restored for the next use without requiring any user intervention. However, the mechanism does not move the blister backward. It can be seen from the disclosure above, that the device according to the present invention can be operated by a simple single push action of the user. When the lid is closed, the device (11) is set up automatically and is restored for the next use.

The linear motion of the trigger is the sliding in-out motion of the trigger on any direction, including those on the x and y axes. This direction is determined according to the design of the device.

The term gear set covers the main drum, transmission wheel, blister cover lower, central, and upper winding gears, and the additional gears, wherein other wheels and gears to be included in the basic elements of the device are also covered under this term.

In result, an inhaler device is obtained with the embodiment disclosed above, this device being extremely accurate, reliably-operating, and providing advantages in terms of cost and volume, wherein the force required to operate the device and exerted to the components of the mechanism thereof is reduced. An actuator plate (15) and a transmission wheel (17) is used in place of a gear set between the trigger (2) and the main drum (5) to provide these advantages. The force transfer generated by means of the actuater plate without leading to any loss provides a substantial advantage in the push force required to slide in the trigger.

The design of components used may be varied in alternative embodiments according to the type of device being produced. In result, the protection scope of the present invention is set forth in appended claims and cannot be restricted to the illustrative disclosures given above, under the detailed description. It is obvious that a person skilled in the relevant art can produce similar embodiments under the light of the foregoing disclosures, without departing from the main principles of the present invention.

The invention claimed is:

1. A dry powder inhaler device comprising a body, a trigger moving on an axial/linear direction in the body, a main drum into which a blister strip having drug-carrying cavities is placed, a gear set, wherein the gear set enables a drug in the next cavity of the blister strip to be administered by rotating the main drum and around which a protective layer or cover of the blister strip is wound, and additional gears in connection with the main drum and around which a main layer of the blister strip is wound, said device further comprising an actuator plate having a first end connected to the trigger and a second end comprising a socket with a size sufficiently large to receive a transmission wheel therein, a series of teeth which are aligned in the socket of the actuator plate on the axial/linear direction in which the trigger is moved, and a transmission wheel connected to the teeth provided in the socket for converting the axial/linear motion of the trigger into a rotational motion of the transmission wheel and transferring this rotational motion to the main drum, wherein the main drum is disposed on and substantially coaxially with the transmission wheel, wherein the transmission wheel meshes with the series of teeth aligned in the socket of the actuator plate.

2. The dry powder inhaler device according to claim 1, comprising barriers on the inner surface of the body to restrict the amount of displacement of the actuator plate.

3. The dry powder inhaler device according to claim 1, wherein the transmission wheel further comprises a toothless surface section.

4. The dry powder inhaler device according to claim 1, wherein the actuator plate is disposed between the main drum and the trigger.

5. The dry powder inhaler device according to claim 1, comprising a pretensioned spring which restores the trigger to its initial position after the trigger is pushed in axially/linearly and released by a user.

6. The dry powder inhaler device according to claim 1, wherein the series of teeth aligned in the socket of the actuator plate is located along a first edge of the actuator plate, and the actuator plate further comprises a toothless edge substantially opposite to the first edge.

7. The dry powder inhaler device according to claim 1, wherein during a movement of the trigger axially/linearly in and out of the inhaler device, the transmission wheel rotates in two directions at different times and the main drum rotates in one direction.

8. The dry powder inhaler device according to claim 7, further comprising a pretensioned spring which restores the trigger to its initial position after the trigger is pushed in axially/linearly and released by a user.

9. The dry powder inhaler device according to claim 1, wherein the transmission wheel further comprises teeth that mesh with the series of teeth aligned in the socket for converting the axial/linear motion of the trigger into a rotational motion of the transmission wheel.

10. The dry powder inhaler device according to claim 1, wherein the transmission wheel further comprises a central cylindrical member comprising two curved elements substantially opposite to each other.

11. The dry powder inhaler device according to claim 7, wherein the transmission wheel further comprises a central cylindrical member comprising two curved elements substantially opposite to each other.

* * * * *